United States Patent [19]
Draus

[11] Patent Number: 5,189,901
[45] Date of Patent: Mar. 2, 1993

[54] DENSITOMETER CALIBRATION APPARATUS AND METHOD

[75] Inventor: Edward T. Draus, Walsenburg, Colo.

[73] Assignee: Atlantic Richfield Company, Los Angeles, Calif.

[21] Appl. No.: 566,937

[22] Filed: Aug. 13, 1990

[51] Int. Cl.$^5$ .......................................... G01D 18/00
[52] U.S. Cl. .......................................... 73/1 R
[58] Field of Search .......................................... 73/1 R

[56] References Cited

U.S. PATENT DOCUMENTS

| | | | |
|---|---|---|---|
| 2,179,892 | 11/1939 | Lindblad | 73/382 R |
| 3,298,221 | 1/1967 | Miller et al. | 73/32 A |
| 3,320,791 | 5/1967 | Banks | 73/1 R X |
| 4,570,476 | 2/1986 | Davis | 73/1 R |
| 4,694,679 | 9/1987 | Woods | 73/1 R |
| 4,699,002 | 10/1987 | Rockley | 73/32 R X |
| 4,745,807 | 5/1988 | O'Neill | 73/434 |

Primary Examiner—Tom Noland
Attorney, Agent, or Firm—Michael E. Martin

[57] ABSTRACT

A densitometer calibration apparatus includes an enclosure for a pressure vessel which may be submerged in a water bath within the enclosure and through which a control fluid is circulated by a pump and a closed loop conduit arrangement to provide continuous steady state circulation of a fluid whose density is used for calibration. A second flow loop including a pump and a pycnometer are in communication with the pressure vessel for filling the pycnometer with a quantity of fluid to be weighed for density comparison with the densitometer reading. Fluid is circulated through the pressure vessel while it is submerged in the temperature controlled water bath and the pycnometer is filled and removed for weight determination at selected operating pressures and temperatures to obtain densitometer calibration parameters.

13 Claims, 2 Drawing Sheets

DENSITOMETER CALIBRATION APPARATUS AND METHOD

BACKGROUND OF THE INVENTION

1. Field of the Invention

The present invention pertains to an apparatus and method for calibrating or confirming the accuracy of densitometers used in conjunction with fluid flow systems, including pipelines.

2. Background

In many pipelining operations and other fluid handling systems, densitometers are utilized to control processes and to confirm or determine mass flow rates. Field calibration of remotely located pipeline densitometers is desirable and necessary to set tariffs and control flow rates. The calibration of a densitometer is not easily accomplished under field conditions due to remote locations of the densitometer in its normal installation. Accordingly, there has been a need to improve densitometer calibration devices and methods and to provide a system which can be taken into the field and used to accurately calibrate densitometers, particularly those used in conjunction with pipelining operations.

SUMMARY OF THE INVENTION

The present invention provides an apparatus and method for calibrating or confirming the accuracy of a densitometer, including those types typically used in conjunction with pipelining operations.

In accordance with one important aspect of the present invention, there is provided an apparatus for calibrating a densitometer using the fluid from the pipeline or process system in conjunction with which the densitometer is normally used and wherein the accuracy of the densitometer may be readily determined for a selected set of operating conditions.

In accordance with another important aspect of the present invention, a densitometer calibration apparatus is provided which is essentially self-contained, may be controlled to accurately maintain steady state temperature and pressure controlled operating conditions to improve calibration accuracy.

The present invention advantageously includes, in combination, a self-contained enclosure or box which may be partially filled with a liquid such as water to maintain a uniform temperature surrounding a pressure vessel and associated piping so that accurate temperature control of a fluid being circulated through the pressure vessel is obtained for making accurate fluid density measurements.

In accordance with yet a further aspect of the present invention, a densitometer calibration apparatus is provided wherein a pycnometer is provided in a flow loop including a pressure vessel simulating a section of pipeline in which the densitometer is disposed and wherein the pycnometer may be filled with working fluid at working pressure and temperature conditions and then readily removed from the controlled environment for measurement of the weight of a known quantity of fluid disposed in the pycnometer.

In accordance with yet a further aspect of the present invention, a densitometer calibration system is provided and which is adapted to more accurately calibrate or measure the performance of certain types of densitometers.

Those skilled in the art will recognize the above-mentioned advantages and features of the present invention together with other superior aspects thereof upon reading the detailed description which follows in conjunction with the drawing.

DESCRIPTION OF PREFERRED EMBODIMENTS

Figure 1:
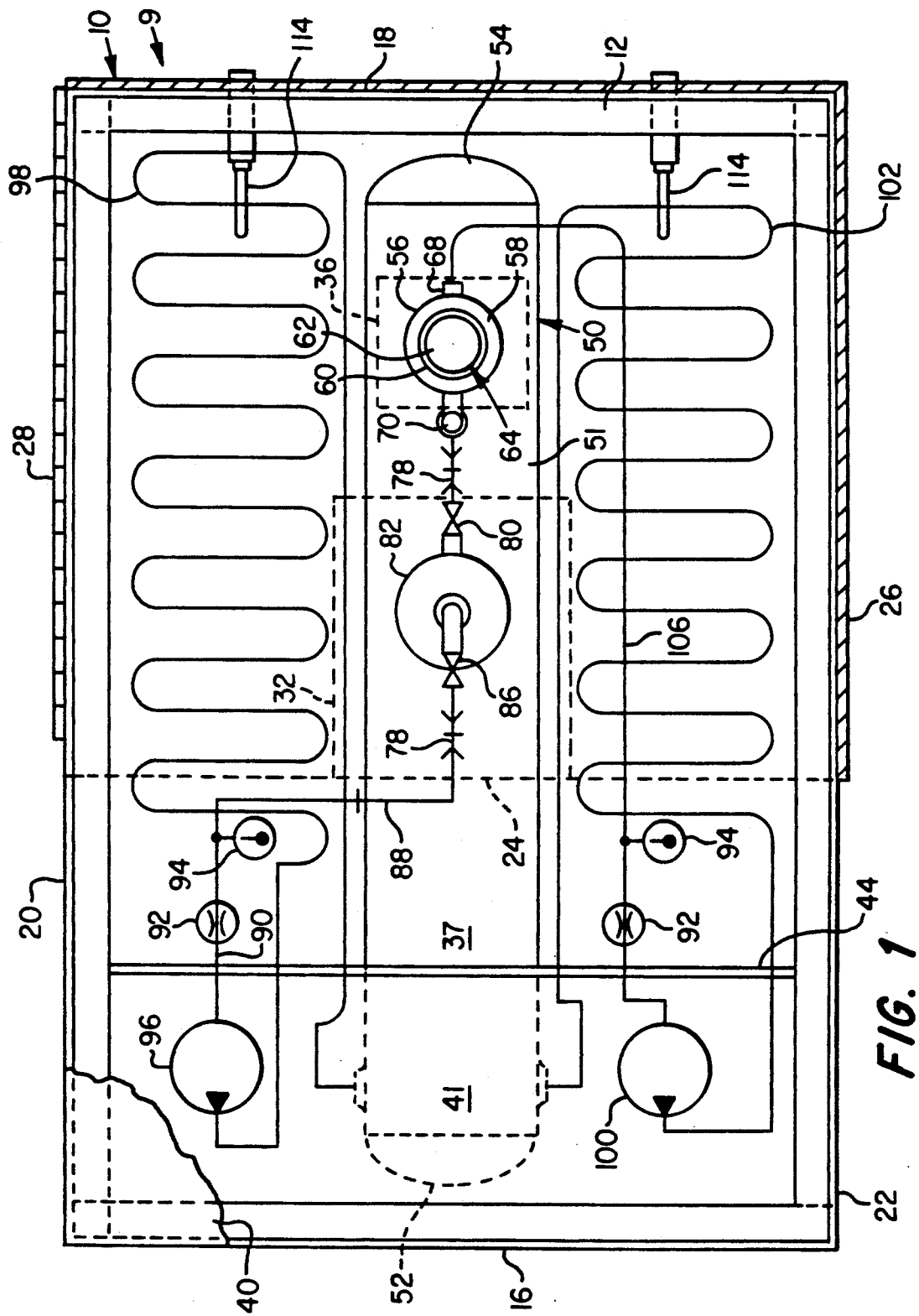
FIG. 1 is a plan view in somewhat schematic form of the apparatus of the present invention.

In the description which follows, like parts are marked throughout the specification and drawing with the same reference numerals, respectively. The drawing figures are not to scale and certain features are shown in generalized or schematic form in the interest of clarity and conciseness.

Figure 2:
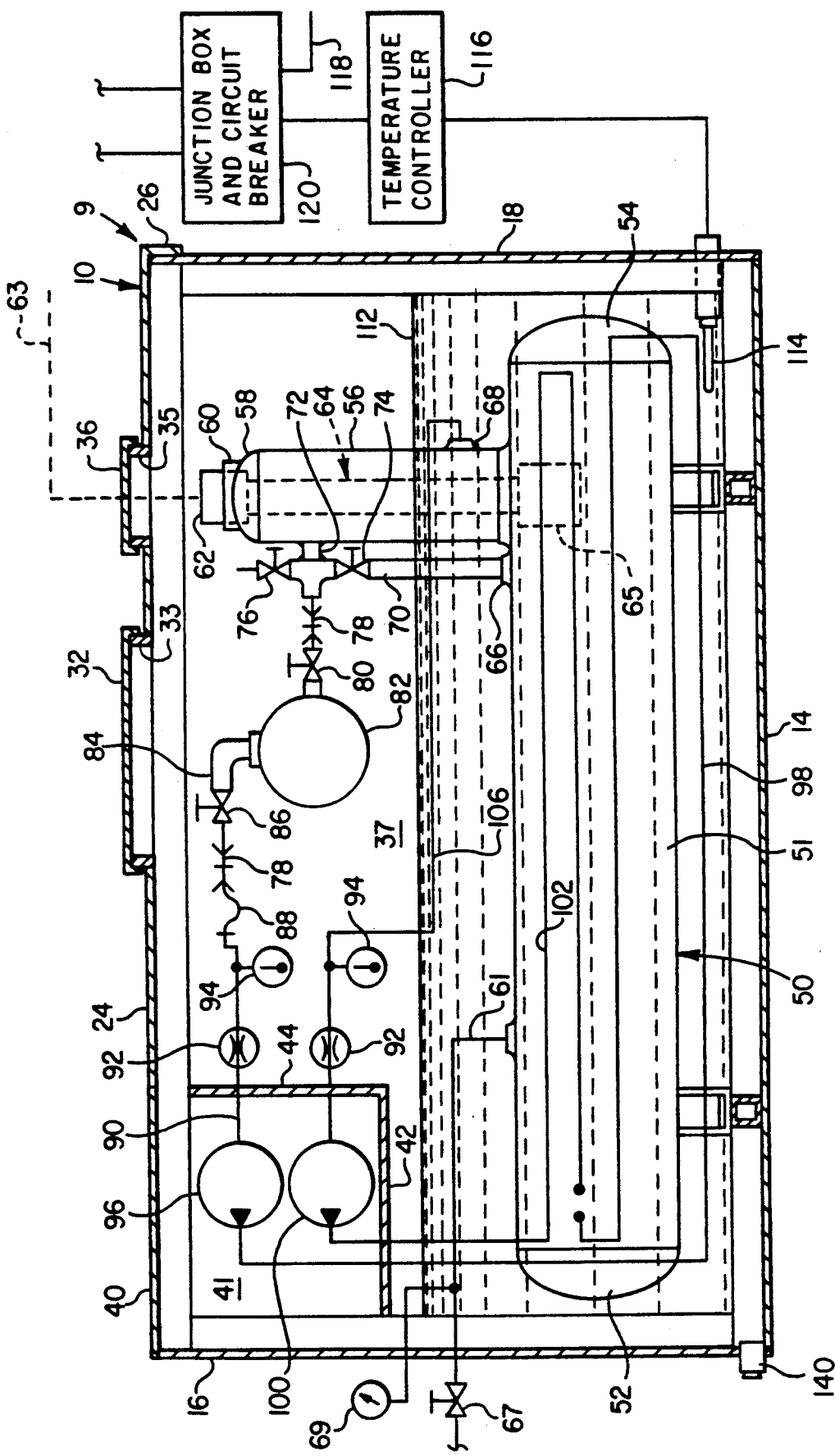
FIG. 2 is a side elevation view, partially sectioned, and also in somewhat schematic form of the apparatus of the present invention.

Referring to the drawing, FIGS. 1 and 2 illustrate a densitometer calibration apparatus 9 including a generally rectangular box-type enclosure 10 comprising a part of the apparatus of the invention. The enclosure 10 includes a generally rectangular tubular frame 12 forming support for a bottom wall 14, opposed end walls 16 and 18, opposed side walls 20 and 22 and a top wall 24 which includes a main access door 26. The door 26 is hinged to the top edge of the side wall 20 at hinge means 28. An access door 32 covers an opening formed by a rectangular coaming 33 formed on the door 26 and yet a second access door 36 is adapted to cover an opening formed by a coaming 35 also in the door 26. The doors 32 and 36 are hinged to their respective coamings by conventional hinge means to provide access to the interior space 37 of the enclosure 10 without opening the main access door 26.

A second portion of the top wall 24 is indicated by the numeral 40 and comprises a removable plate suitably secured to the frame 12 and removable to provide access to a space 41 defined by interior closure walls 42 and 44. The space 41 is configured to provide support for certain motor driven pumps used in the densitometer calibration apparatus and which will be described in further detail herein.

Construction of the enclosure 10 may be obtained by providing the frame 12 made up of generally conventional metal rectangular tube members suitably secured together such as by welding. The bottom wall 14, end walls 16 and 18, and opposed side walls 20 and 22 may be formed of metal plate or a suitable waterproof and preferably thermally insulative material.

Referring further to the drawing, the enclosed space 37 is occupied by a pressure vessel 50 having an elongated, generally horizontally extending cylindrical portion 51 including opposed closure heads 52 and 54. A generally upstanding tower portion 56 of the pressure vessel 50 extends from the top of the portion 51 and includes a closure head 58 formed with a suitable threaded boss 60 for receiving a head part 62 of a conventional pipeline densitometer 64. The densitometer 64 extends within the tower 56 and into the interior of the pressure vessel 50 to simulate its position in a pipeline. The pressure vessel 50 is adapted to have process fluid circulated therethrough by way of an inlet conduit 61, provided with a suitable pressure gauge 69 whereby the pressure of the fluid residing in the pressure vessel may be measured, and dual outlet ports 66 and 68, the latter being formed at the base of the tower portion 56. The port 66 is connected to a conduit 70 which is preferably of rigid metal pipe and is supported by a brace 72 also connected to the tower 56. A shut-off valve 74 is interposed in the conduit 70 and a vent valve 76 is in communication with the conduit 70.

The conduit 70 is also in communication with a quick disconnect type coupling 78, one side of which is connected to a shut-off valve 80 secured to a pycnometer 82. The pycnometer 82 is thus supported in the position shown in FIG. 2 by the braced conduit 70. The pycnometer 82 has an outlet conduit 84 fitted with a suitable shut-off valve 86 and a second quick disconnect type coupling 78. The second coupling 78 is connected to a flexible conduit section 88 which is connected to a conduit 90 having a flowmeter 92 and a temperature sensor 94 interposed therein. The conduit 90 is connected to a pump 96, disposed in the space 41, for circulating fluid by way of a conduit 98, disposed in the space 37 to the end of the pressure vessel 50 adjacent the closure head 52. Fluid disposed in the pressure vessel 50 may be circulated therethrough by the pump 96 and through the pycnometer 82 on a continuous basis.

The apparatus 9 includes a second fluid circulating pump 100 disposed in the space 41 and driven, like the pump 96, by suitable electric motor means, not shown. The pump 100 is connected to a conduit 102 which is disposed in the space 37 and is connected to the pressure vessel 50 also, at the end adjacent the closure head 52 and, as shown in FIG. 1, opposite the conduit 98. The fluid is circulated through the pressure vessel 50 by the pump 100 and is discharged therefrom by way of a conduit 106 having interposed therein a flowmeter 92 and a temperature sensor 94. The flowmeters 92 and sensors 94 may be provided with suitable remote readout devices, not shown, on the exterior of the enclosure 10. The conduit 106 is connected to the pressure vessel 50 at the fitting 68 at the base of the tower section 56. Accordingly, fluid being circulated through the pressure vessel 50 flows continuously over the densitometer 64, having its sensing head 65 disposed within the generally horizontally extending vessel portion 51.

As illustrated in FIG. 1, the conduits 98 and 102 have a generally serpentine configuration to provide sufficient conduit length for maintaining steady state temperature conditions of the fluid being circulated through the conduits by the pumps 96 and 100. In order to maintain a selected temperature of the fluid being circulated through the pressure vessel 50, the enclosure 10 may be partially filled with a heat exchange liquid, such as water, generally indicated by the numeral 112. Water is introduced into the space 37 to a depth which provides for complete covering of the vessel portion 51 and the serpentine heat exchange conduits 98 and 102. The water 112 may be temperature controlled by suitable heating elements 114 of the electrical resistance type which are connected in circuit with a temperature controller 116 supplied with electrical power from a suitable source, not shown, by way of conductor means 118 and by way of a junction and circuit breaker box 120. The water 112 may be circulated through the space 37 by a suitable sump pump, not shown, to enhance the uniformity of the temperature of the water. A suitable temperature sensor, not shown, is also provided for sensing the temperature of the water 112 and controlling the operation of the heating elements 114 in a conventional manner.

The construction of the vessel 50 may be carried out using conventional engineering practices and materials for pressure vessels subjected to fluid pressures and temperatures within the operating range of the pipelines whose densitometers are to be calibrated. The pumps 96 and 100 may be of a type suitable for the fluid being circulated. If the fluid being circulated is liquid carbon dioxide, for example, the pumps 96 and 100 may be of a so-called magnetic gear type manufactured by Micromotion, Inc., Boulder, Colo. The apparatus illustrated and described above is particularly suitable for calibrating a densitometer of a type manufactured by Sarasota Automation Company, Houston, Tex., although the apparatus may be used in conjunction with other densitometer devices. The flow meters 92 and the temperature sensors 94 may be of conventional types as well as the heating elements 114.

The operation of the apparatus 9 in accordance with the improved method of the present invention will now be described. Prior to commencing calibration of a densitometer such as the densitometer 64, the apparatus 9 would be suitably disposed in proximity to a pipeline meter station or the like whose densitometers are to be measured. Water 112 would be added to the space 37 to at least completely submerge the conduits 98 and 102 and the pressure vessel portion 51. The controller 116 would be set to the preferred temperature and heating elements 114 turned on to heat the water to such temperature. A densitometer 64 to be calibrated would be removed from the pipeline metering system and installed in the tower 56 through the door 36. The pycnometer 82 would be removed from the circuit of the pump 96 by uncoupling the quick disconnect couplings 78 and removing the pycnometer from the space 37 through the opening 33. The pycnometer 82 would be purged of fluids other than air at ambient pressures and temperatures and at such conditions, the pycnometer tare weight would be obtained. The pycnometer 82 would then be reinstalled in the circuit illustrated in FIGS. 1 and 2. Thanks to the arrangement of the conduit 70, the bracing 72, the couplings 78 and the valves 80 and 86, the pycnometer 82 is supported in the space 37 and is conveniently removed from the system or reinstalled in the system as described above. The quick disconnect couplings 78 are of the self-sealing type to prevent loss of fluid from the pycnometer 82 or from the system. The order of the steps of the aforedescribed procedure is not important but all steps must be completed prior to further steps in the process.

The pressure vessel 50 is suitably connected to a source of fluid whose density is to be used to calibrate the densitometer 64. Preferably the fluid is the same as being flowed through the pipeline or other fluid process system from which the densitometer was removed. Accordingly, the conduit 61 would be suitably connected to the pipeline, for example, and fluid from the pipeline flowed into the pressure vessel 50 by way of the conduit while monitoring pressure at the gauge 69. When a sufficient amount of fluid is piped into the pressure vessel 50, the valve 67 would be closed and the pumps 96 and 100 started to circulate fluid through the pressure vessel and the conduits connected to the respective pumps. Complete purging of the pressure vessel 50 may be carried out by venting fluid through the vent valve 76.

When the temperature of the water bath provided by the water 112 has stabilized at a constant value and steady state conditions of fluid being circulated by the pumps 96 and 100 is obtained, the pump 96 is stopped, the pycnometer valves 80 and 86 closed and the pycnometer 82 is decoupled from the system and weighed to obtain the density of the fluid at the selected pressure and temperature condition. This density would be compared with a fluid density reading obtained from the densitometer 64 installed in the pressure vessel 50. The densitometer 64 would be connected to its own readout circuit, not shown, by way of conductor means 63 or a readout device built into the head part 62. The pycnometer 82 would then be reinserted in the system as illustrated. Plural operating conditions are preferably carried out in order to determine calibration constants for the densitometer 64. For example, at least four selected operating pressures and/or temperatures within the pressure vessel 50 would be established using a suitable pressure controller, not shown, or by venting fluid from the pressure vessel through the valve 76. At each of the plural pressure and/or temperature conditions within the pressure vessel 50, operating temperature of the fluid as determined by the temperature sensor 94 in circuit with the pumps 96 or 100 would be obtained and of course, the density of fluid in the pycnometer would be determined. Fluid is advantageously circulated through the pressure vessel 50 by the pump 100 during shutdown of the pump 96 and removal of the pycnometer 82 from the system so as to maintain steady state conditions of the fluid being measured.

When the calibration procedure has been completed, fluid is vented from the pressure vessel 50 down to a suitable pressure so that the densitometer 64 can be removed from the tower 56 and replaced with another densitometer to be calibrated, for example.

Thanks to the provision of the pressure vessel 50 in the water bath enclosure 10 and the constant temperature provided by the water bath as well as the flow circulating pump 100 and its respective inlet and discharge conduit circuit, rapid and accurate multi-step calibration procedures may be carried out with the apparatus of the present invention. Upon completion of the calibration procedure, the water 112 may be drained through a suitable fitting 140 disposed at a low point in the enclosure 10.

Although a preferred embodiment of a densitometer calibration apparatus and method have been described hereinabove, those skilled in the art will recognize that various substitutions and modifications may be made to the embodiments disclosed without departing from the scope and spirit of the invention as recited in the appended claims.

What is claimed is:

1. An apparatus for calibrating a densitometer and the like comprising:
   means forming an enclosure defining a space for at least partially filling said space with a temperature controlled liquid bath;
   a pressure vessel disposed in said space including means for receiving a densitometer to be disclosed in said pressure vessel, for measuring the density of a fluid in said pressure vessel;
   first pump means for circulating a fluid through said pressure vessel whose density is to be measured;
   a flow circuit connected to said pressure vessel including a pycnometer removably connected to said flow circuit for receiving a quantity of said fluid at the controlled temperature condition and for removal from said flow circuit to be weighed to determine the density of said fluid at said temperature controlled condition; and
   second pump means for circulating said fluid through said pycnometer.

2. The apparatus set forth in claim 1 including:
   quick disconnect coupling means connected to said pycnometer and to conduit means in said flow circuit for rapidly disconnecting and reconnecting said pycnometer with respect to said apparatus.

3. The apparatus set forth in claim 1 including:
   flow meter means interposed in said flow circuit for determining a flow rate of fluid through said flow circuit.

4. The apparatus set forth in claim 1 including:
   temperature sensor means interposed in said flow circuit for measuring the temperature of fluid being circulated through said pressure vessel.

5. The apparatus set forth in claim 1 wherein:
   said pressure vessel includes an elongated, horizontally extending portion and a generally vertically extending tower portion for receiving said densitometer so as to extend therefrom into said horizontally extending portion for sensing the density of fluid being circulated through said pressure vessel.

6. The apparatus set forth in claim 1 wherein:
   said first pump means is disposed in a circuit including heat exchange conduit means disposed in said liquid bath for maintaining a preselected temperature of said fluid being circulated through said pressure vessel.

7. The apparatus set forth in claim 1 wherein:
   said flow circuit includes heat exchange conduit means disposed in said liquid bath for maintaining a predetermined temperature of fluid being circulated through said flow circuit by said second pump means.

8. An apparatus for calibrating a densitometer and the like comprising:
   means forming an enclosure defining a space for at least partially filling said space with a temperature controlled liquid bath;
   a pressure vessel disposed in said space including means for receiving a densitometer to be disposed in said pressure vessel for measuring the density of a fluid in said pressure vessel;
   a first flow circuit connected to said pressure vessel including a pycnometer removably connected to said first flow circuit for receiving a quantity of said fluid at a preselected temperature condition and for removal from said first flow circuit to be weighed to determine the density of said fluid at said temperature controlled condition and heat exchange conduit means disposed in said liquid bath for maintaining said preselected temperature of said fluid being circulated through said first flow circuit; and
   pump means for circulating said fluid through said first flow circuit.

9. The apparatus set forth in claim 8 including:
   quick disconnect coupling means connected to said pycnometer and to conduit means in said flow circuit for rapidly disconnecting and reconnecting said pycnometer with respect to said apparatus.

10. The apparatus set forth in claim 8 including:
    flow meter means interposed in said flow circuit for determining a flow rate of fluid through said flow circuit.

11. The apparatus set forth in claim 8 including:
a second flow circuit connected to said pressure vessel for circulating said fluid therethrough and including a heat exchange conduit disposed in said liquid bath and pump means interposed in said second flow circuit.

12. A method for calibrating a densitometer and the like for pipeline or process flow systems, said method comprising the steps of:
providing an apparatus including an enclosure defining a space at least partially filled with a temperature controlled liquid bath, a pressure vessel disposed in said space and including means for receiving a densitometer, a flow circuit connected to said pressure vessel including a pycnometer and coupling means for connecting said pycnometer in and removing said pycnometer from said flow circuit with a quantity of fluid to be measured at a particular pressure and temperature condition;
connecting said pressure vessel to a source of fluid whose density is to be measured and flowing said fluid through said pressure vessel and said pycnometer at a constant temperature as determined by the temperature of said liquid bath;
retaining a quantity of fluid whose density is to be measured in said pycnometer and removing said pycnometer from said apparatus;
weighing said pycnometer to determine the density of fluid being circulated through said pressure vessel and comparing the density determined by said pycnometer with the density measured by said densitometer.

13. The method set forth in claim 12 including the step of:
continuing to circulate fluid through said pressure vessel while said pycnometer is removed therefrom by providing second pump means and a flow circuit associated therewith for circulating said fluid through said pressure vessel.

* * * * *